United States Patent
Hegstrom et al.

(10) Patent No.: US 9,804,087 B2
(45) Date of Patent: Oct. 31, 2017

(54) HEMISPHERICAL SCANNING OPTICAL SCATTEROMETER

(71) Applicant: ScatterMaster LLC, Tucson, AZ (US)

(72) Inventors: Eric Loren Hegstrom, Tucson, AZ (US); John Clyde Stover, Tucson, AZ (US)

(73) Assignee: SCATTERMASTER, LLC, Tucson, AZ (US)

( * ) Notice: Subject to any disclaimer, the term of this patent is extended or adjusted under 35 U.S.C. 154(b) by 62 days.

(21) Appl. No.: 14/291,281

(22) Filed: May 30, 2014

(65) Prior Publication Data

US 2014/0362377 A1 Dec. 11, 2014

Related U.S. Application Data

(60) Provisional application No. 61/833,858, filed on Jun. 11, 2013.

(51) Int. Cl.
G01N 21/47 (2006.01)

(52) U.S. Cl.
CPC ....... *G01N 21/474* (2013.01); *G01N 21/4738* (2013.01); *G01N 21/47* (2013.01); *G01N 2021/4711* (2013.01); *G01N 2021/4723* (2013.01)

(58) Field of Classification Search
CPC .... G01N 21/47; G01N 21/4738; G01N 21/49; G01N 21/57; G01N 2021/4711; G01N 2021/4723
USPC ......................................... 356/446
See application file for complete search history.

(56) References Cited

U.S. PATENT DOCUMENTS

| 6,249,751 | B1* | 6/2001 | Asaba et al. | 702/76 |
| 6,642,063 | B2* | 11/2003 | Mundt | G01N 21/9501 257/E21.53 |
| 6,833,913 | B1* | 12/2004 | Wolf et al. | 356/237.2 |
| 6,914,684 | B1* | 7/2005 | Bolash et al. | 356/600 |
| 2008/0304070 | A1* | 12/2008 | Bonnet | 356/446 |

* cited by examiner

*Primary Examiner* — Kara E Geisel
*Assistant Examiner* — Shawn Decenzo
(74) *Attorney, Agent, or Firm* — Edward Weck

(57) ABSTRACT

A hemispherical scanning optical scatterometer and method for its use for measuring scattered radiation, with a reflected scatter measurement laser, and/or a transmitted scatter measurement laser, an array of optical detectors, a computer controlled system to rotate the array of optical detectors, an electronic system, a computer interface and a computer for processing the signal.

20 Claims, 7 Drawing Sheets

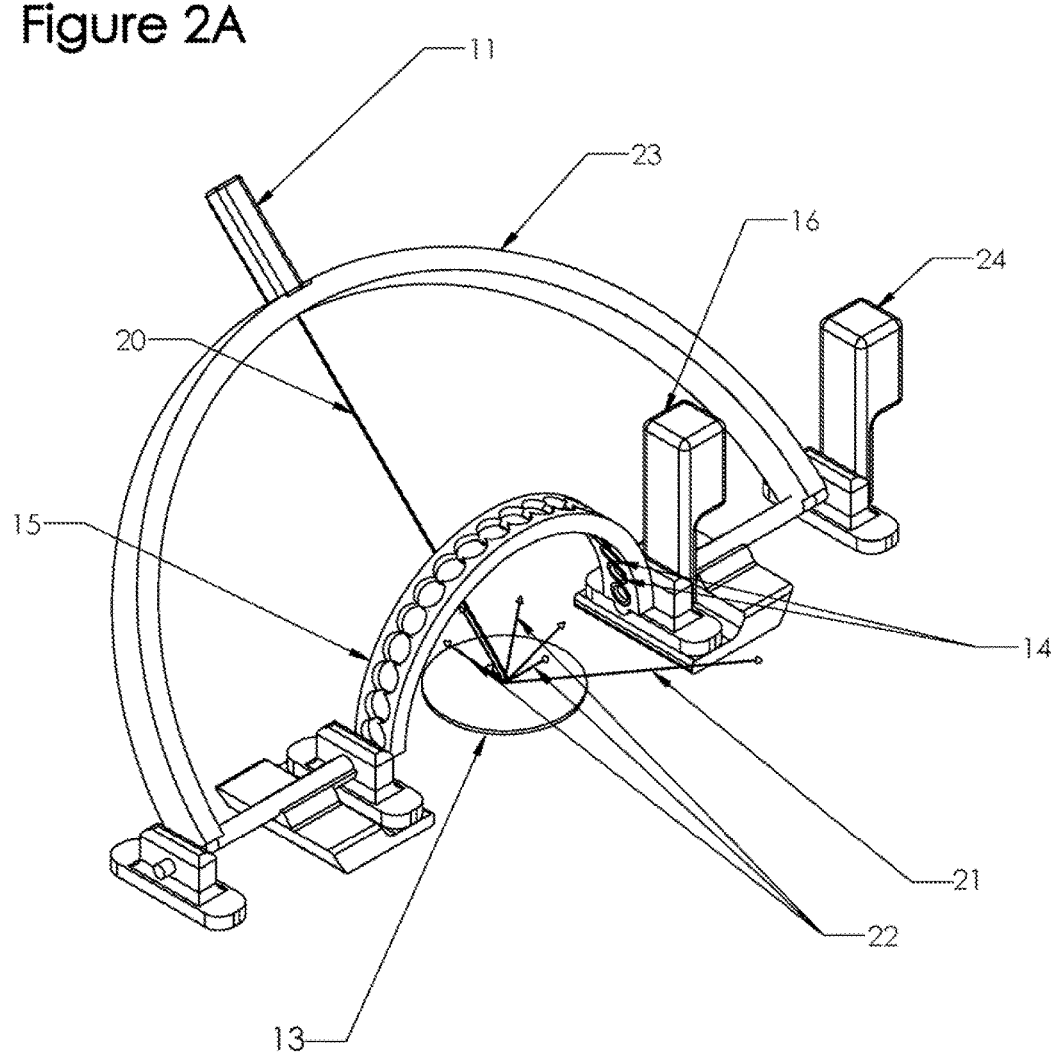

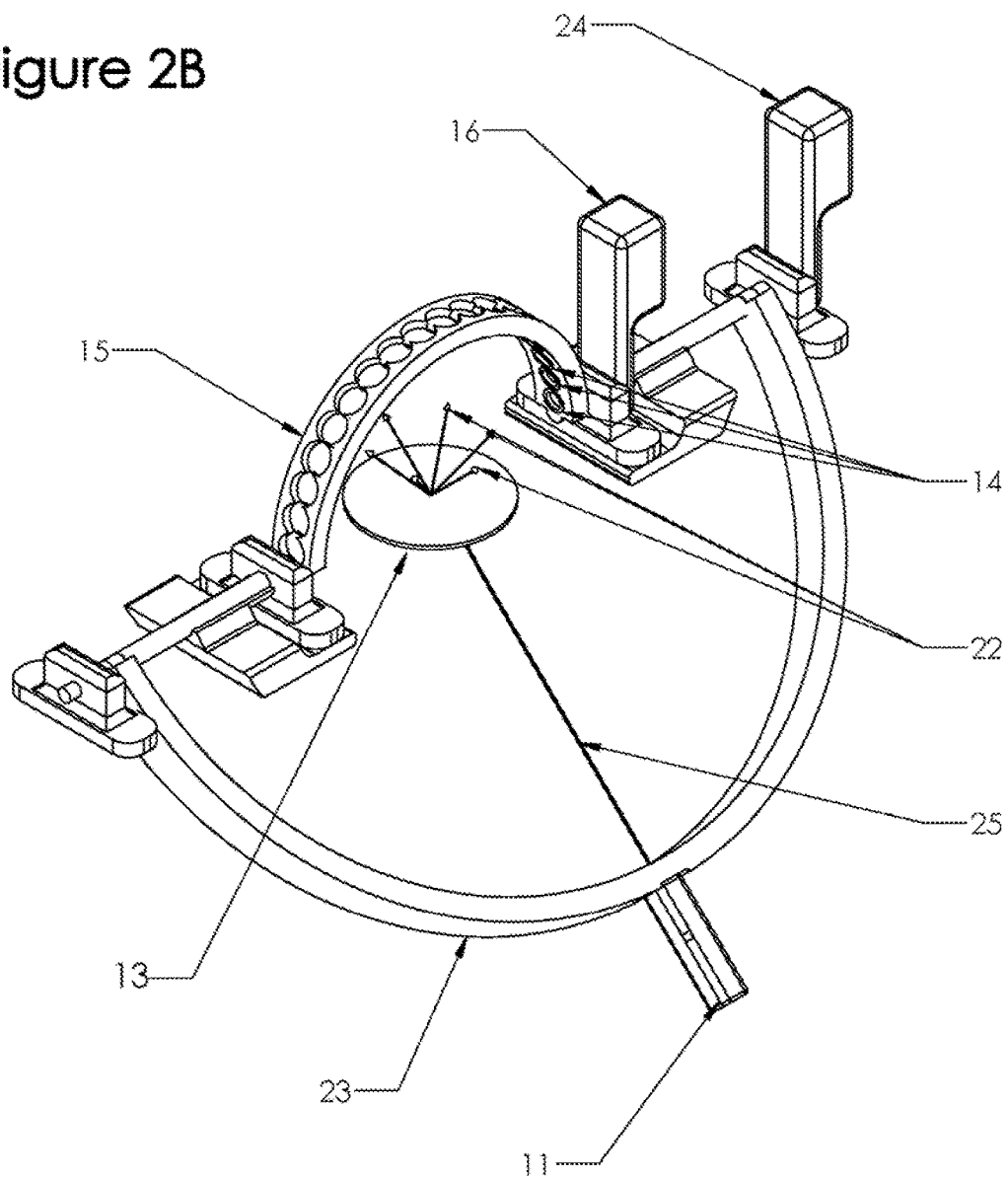

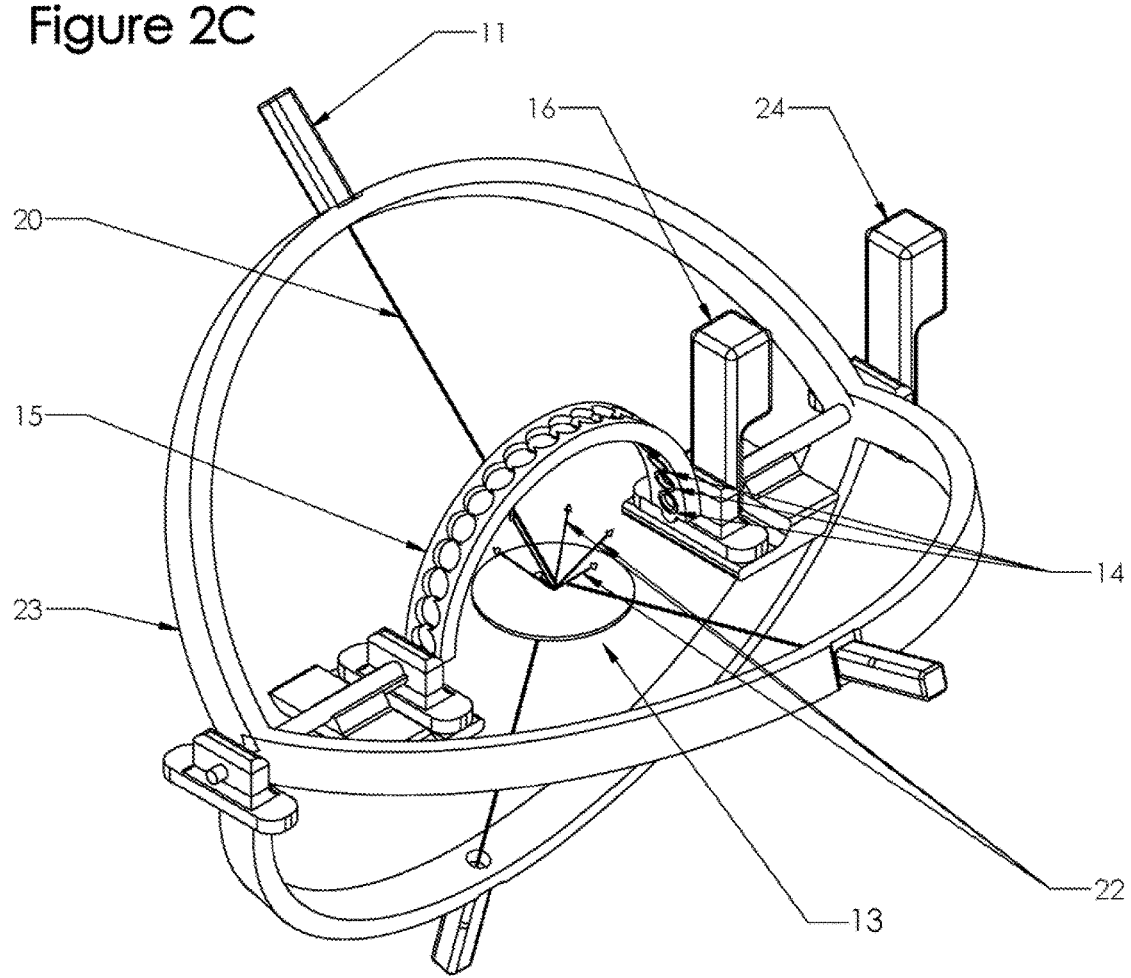

HEMISPHERICAL SCANNING OPTICAL SCATTEROMETER

BENEFIT OF PRIORITY

This application claims the benefit of priority of prior filed U.S. application Ser. No. 61/833,858 filed Jun. 11, 2013, which is herein incorporated by reference in its entirety.

BACKGROUND OF THE INVENTION

Summary of the Invention

The present invention relates to a scatterometer that can measure and quantify the scattering of light or other radiation from or through a test sample at a plurality of locations over a complete hemisphere.

Description of the Related Art

A scatterometer is a device that measures the intensity of light scattered by an object. For example, a theoretical perfect mirror would perfectly reflect a laser beam in a single direction. In reality the properties of the test sample (material properties as well as surface and body structure) will cause some portion of the light to be scattered in different directions known as scatter angles. As a result the scatter signal can vary by as many as fourteen decades over the hemisphere. It will normally peak in the direction associated with the reflected (or transmitted) specular beam, where it can change by several decades over just a few degrees. For many samples a serious technical issue is getting accurate measurements in both the specular and non-specular regions. Scatter can be measured in either the reflective hemisphere, or the transmissive hemisphere, or both. Scatterometers sample the reflected or transmitted light in steps that are close enough that software can estimate the light intensity between measurement locations. Typically more measurements are made close to the specular beam, where light levels are changing faster per unit angle, than at higher scatter angles. Most scatterometers in use today measure just a fraction of one hemisphere and are often limited to just the incident plane. Measurements are recorded as a function of angular position on the hemisphere in units that are defined by international standards. These scatter measurements are used in a variety of research, design, and manufacturing processes to directly quantify the optical properties of materials. In addition to measuring the optical performance of a material, scatter measurements are used to infer other physical information about the material composition and structure (such as surface roughness).

The prior art teaches a variety of systems that scan a single detector or employ multiple fixed detectors. These include systems that:

- sample scatter in the incident plane and gather enough data to calculate in-plane scatter, for example, U.S. Pat. No. 5,241,369;
- sample hemispherical scatter with a single detector and (slowly) sample enough data to calculate hemispherical scatter, for example, U.S. Pat. No. 7,349,096;
- use screens and/or cameras to sample scatter over a limited portion of the hemisphere allowing scatter to be quickly calculated but only for a limited dynamic range, for example, U.S. Pat. No. 7,248,368; or
- use complex systems of large fiber-optic bundles, or multiple fixed detectors, to coarsely sample hemispherical scattered light, for example, U.S. Pat. No. 5,313,542.

In general these systems do not take enough data samples to calculate scatter over most of the hemisphere and/or are not able to cover the large dynamic range of scatter associated with optical surfaces. The fixed multiple detector systems have dynamic range problems when the incident angle is changed. The moving single detector systems have problems with measurement speed.

SUMMARY OF THE INVENTION

Apparatus and methods in accordance with the present inventions may resolve many of the needs and shortcomings discussed above and will provide additional improvements and advantages as will be recognized by those skilled in the art upon review of the present disclosure.

The hemispherical scanning optical scatterometer apparatus and methods of this invention allow rapid measurement over the complete (or nearly complete) hemisphere using a scanning array of optical detectors connected to electronics capable of reacting over a large dynamic range. The scanning geometry employs a set of small diameter high resolution detectors to scan through the specular reflection (or transmission) and the region near the specular reflection (or transmission) even when the incident angle is changed. The rest of the detectors are used to gather the lower intensity scattered light farther away from the specular (or transmission) direction. In this way no one detector is confronted with a scatter signal that changes by more than about seven orders of magnitude. This results in improved hemispherical coverage, increased dynamic range and increased measurement speed. The dynamic range of measurement over the hemisphere exceeds ten decades and the measurement speed for a sample is in the 1-30 second range depending on the sample and how many measurements are taken. In addition, scatter into both the reflected and transmitted hemispheres can be sampled.

The scatterometer apparatus may take a variety of geometrical shapes and may include any combination of sizes and packages of detectors. In addition, any combination of detector sizes may be employed. Smaller area detectors are better for measuring larger signals and provide better angular signal resolution as when measuring near the specular reflection (or transmission). Larger area detectors are better for measuring very low level signals and are often employed away from the specular reflection (or transmission).

In the preferred embodiment the nearly complete hemisphere or a partial hemisphere is sampled by larger detectors (typically between 30 and 100 square mm in area) that are located about one to five degrees apart. An additional array of smaller closely spaced detectors (typically between 0.05 and 30 square mm in area) are used to scan the incident plane (the arc containing sample normal and the specular beam), which allows much higher angular resolution of the larger near specular signals.

The detectors may make use of components (tubes or lenses and field stops) that limit the detector field of view to eliminate light arriving from other sources than the illuminated test sample, as shown in FIG. 6.

The signal data is then analyzed by a computer program that converts the measurements to industry standard Bidirectional Reflectance Distribution Function (BRDF) or Bidirectional Transmittance Distribution Function (BTDF) which are jointly referred to as Bidirectional Scatter Distribution Function (BSDF). The software provides multiple options for using and presenting the information including any combination of the following:

1) Three dimensional visualizations of the hemispherical scatter signal may be viewed, rotated, printed, and archived.

2) Virtual detectors may be defined by shape, size and angular location on the scattering hemisphere using the system software. The software will then compute the same signals as would be measured by a physical detector of any shape and location in the scattering hemisphere. These measurements may be used directly or used to facilitate the design of optical instrumentation.
3) Scatter data may be exported in many formats to feed into other software such as optical modeling, lighting simulation, quality control, manufacturing control, etc.
4) Depending on the sample, a variety of material characteristics may be characterized. These include surface roughness, the surface power spectral density function and estimated sizes of discrete surface features such particles and pits.
5) A variety of optical characteristics may be calculated. These include haze, Total Integrated Scatter, specular and diffuse reflectance, and specular and diffuse transmittance.

Any of these types of analysis can be used to generate numerical grades and, when provided with acceptable range values, can drive automated Pass/Fail inspection. Any of the scatter data, derived measurements, numerical grades and/or pass/fail analysis results may be used as feedback for control of scientific, manufacturing or other processes or for quality control inspection.

BRIEF DESCRIPTION OF THE DRAWINGS

All Figures are illustrated for ease of explanation of the basic teachings of the present invention only; the extensions of the Figures with respect to number, position, relationship and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

FIGS. 2A, 2B and 2C of the drawings of the hemispherical scanning optical scatterometer with a movable scatter measurement laser.

DETAILED DESCRIPTION OF THE INVENTION

This invention describes an apparatus and methods for measuring the intensity of specular reflection (or transmission) and scattered radiation over a nearly complete hemisphere or a partial hemisphere employing an array of detectors that are moved (scanned) through the specular reflection (or transmission) and scattered light making a measurement of any and/or all desired scatter angles.

Figure 1:
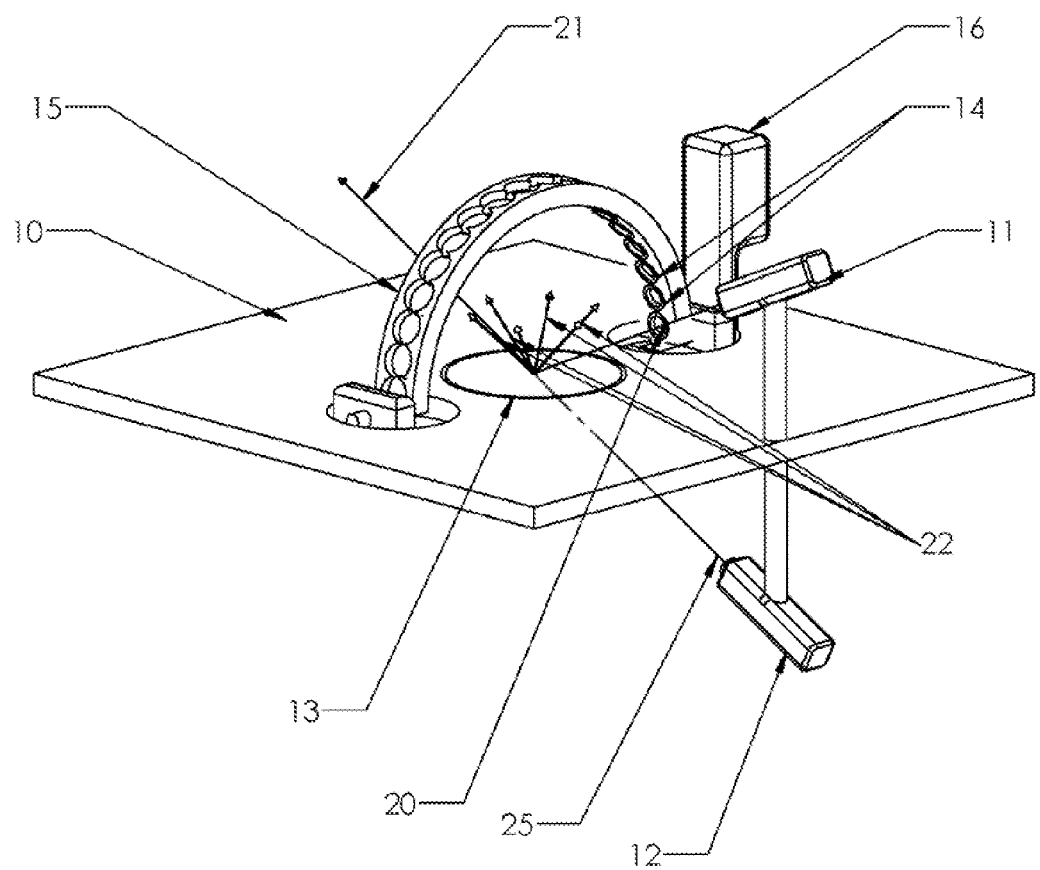
FIG. 1 of the drawings shows a diagram of the hemispherical scanning optical scatterometer with a fixed reflected scatter measurement laser and a fixed transmitted scatter measurement laser.

The present invention provides a first embodiment of a scatterometer 10 and methods for implementing the scatterometer 10. As shown in FIG. 1, the scatterometer 10 includes a reflected scatter measurement laser 11, a transmitted scatter measurement laser 12, a test sample 13, a collection of optical detectors 14 arranged in an arc or a similar shape on an arm 15 and a computer controlled system 16 to rotate the collection of optical detectors 14 through the nearly complete hemisphere or a partial hemisphere of specular reflection (or transmission) and scattered light. As shown in FIG. 8, the scatterometer 10 also includes electronics 17 for logarithmic conversion and amplification of the signal, a computer interface 18 for analog to digital signal conversions and a computer with processing software 19.

As shown in FIG. 1, the reflected scatter measurement laser 11 emits a laser beam 20 that strikes the test sample 13 at an angle of incidence. A specular beam 21 is reflected off the test sample 13 at an equal angle of incidence. The test sample 13 scatters other light at all angles 22 other than the angle of the specular reflection 21. An array of detectors 14 on arm 15 is rotated by a computer controlled system 16 through the complete hemisphere or a partial hemisphere, as shown in FIG. 1. The detectors 14 measure the intensity of both the specular reflection 21 and the light scattered at other angles 22. The signals for each of the detectors 14 are fed through logarithmic conversion and amplifier 17 which is fed into an analog to digital computer interface 18 and then into a computer with analysis software 19, FIG. 7.

As shown in FIG. 1, the transmitted scatter measurement laser 12 emits a laser beam 25 that strikes the test sample 13 at an angle of incidence. A transmission beam 21 exits the sample. The test sample 13 scatters other light at all other angles 22 except the angle of the transmission beam 21. An array of detectors 14 on an arm 15 is rotated by a computer controlled system 16 through the complete hemisphere. The signals for each detector 14 are fed through logarithmic conversion and amplifier 17 which is fed into an analog to digital computer interface 18 and then into a computer with analysis software 19.

Each detector 14 on the arm 15 follows the same semicircular path for all scans. The incident laser may be either the reflected scatter measurement laser 11 or the transmitted scatter measurement laser 12, as shown in FIG. 1 The scattered light may come from different angles from the sample surface reflected scatter measurement laser 11 or a transmitted scatter measurement laser 12. Typically only one of the lasers 11 or 12 is energized at any given time. The detectors 14 follow the same path each time. The detectors 14 may take measurements at different locations on their fixed paths, depending on how the scan is programmed.

Figure 7:
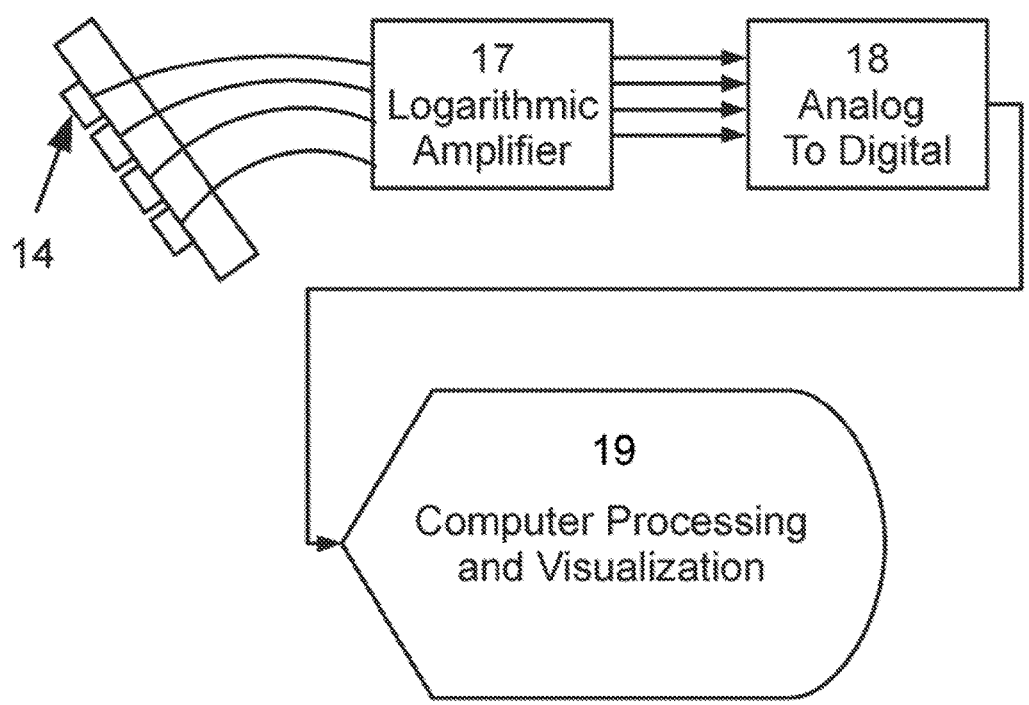
FIG. 7 of the drawings shows a diagram of the information processing of the hemispherical scanning optical scatterometer.

As shown in FIGS. 2A, 2B and 2C a second embodiment of the scatterometer 10 includes a scatter measurement laser 11, a test sample 13, a collection of optical detectors 14 arranged in an arc or a similar shape on an arm 15 and a computer controlled system 16 to rotate the collection of optical detectors 14 through the nearly complete hemisphere or a partial hemisphere of specular reflection (or transmission) and scattered light. The scatter measurement laser 11 is positioned on a second arm 23 and is rotated by a second computer controlled system 24 to a plurality of incident angles and the measurement is repeated at those incident angles. FIG. 2A shows the second arm 23 in a first position during the rotation. FIG. 2B shows the second arm 23 in a third position during the rotation. FIG. 2C shows the second arm in first, second and third positions during the rotation. As shown in FIGS. 2A, 2B and 2C, the movement of the scatter measurement laser 11 controlled by the second computer controlled system 24 defines an incident plane through the changing the incident angles. The movement of the scatter measurement laser 11 is about an axis horizontal to the sample and perpendicular to the incident plane. For mechanical practicality there may be a plurality of second arms 23 and measurement lasers 11. As shown in FIG. 7, the scatterometer 10 also includes electronics 17 for logarithmic conversion and amplification of the signal, a computer interface 18 for analog to digital signal conversions and a computer with processing software 19.

As shown in FIG. 2A, the scatter measurement laser 11 on the second arm 23 emits a laser beam 20 that strikes the test sample 13 at an angle of incidence. A specular beam 21 is reflected off the test sample 13 at an equal angle of incidence. The test sample 13 scatters other light at all other angles 22 except the angle of incidence. The reflected scatter measurement laser 11 on second arm 23 is rotated by a second computer controlled system 24 to a plurality of incident angles and the measurement is repeated at those incident angles, shown in FIGS. 2B and 2C. As shown in FIG. 2A the scatter measurement laser 11 acts as a reflected scatter measurement laser and as shown in FIG. 2B the laser acts as a transmitted scatter measurement laser. For mechanical practicality there may be a plurality of second arms 23 and measurement lasers 11. An array of detectors 14 on arm 15 is rotated by a computer controlled system 16 through the complete hemisphere. The detectors 14 measure the intensity of both the specular reflection (or transmission) beam 21 and the light scattered at other angles 22. The signals for each of the detectors 14 are fed through logarithmic conversion and amplifier 17 which is fed into an analog to digital computer interface 18 and then into a computer with analysis software 19, FIG. 7.

Figure 3:
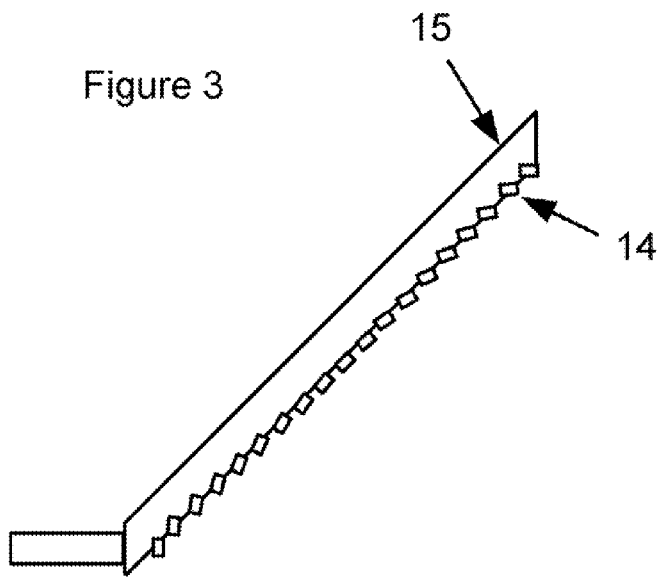
FIG. 3 of the drawings shows a diagram of a linear array of discrete or linear detectors.
Figure 4:
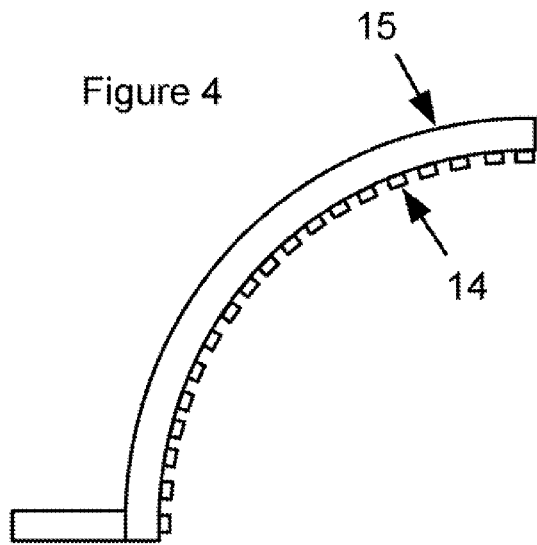
FIG. 4 of the drawings shows a diagram of a curved array of discrete or linear detectors.
Figure 5:
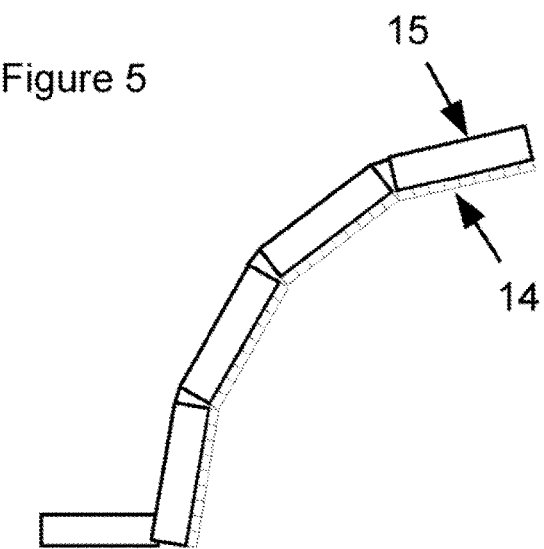
FIG. 5 of the drawings shows a diagram of multiple linear segments of detector arrays.

As shown in FIGS. 3, 4 and 5, the array of detectors may take a variety of geometrical shapes. FIG. 3. shows a linear array of detectors 14. FIG. 4 shows a curved array of detectors 14. FIG. 5 shows a combination of shorter linear arrays of detectors 14 forming a curve.

Figure 6:
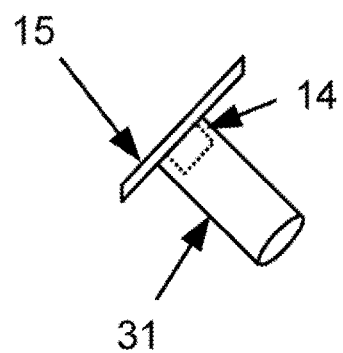
FIG. 6 of the drawings shows a diagram of the limitation of the detector field of view.

As shown in FIG. 6, a thread tube 31 may be used to limit the field of view of the detectors 14.

As shown in FIG. 7, the signals from the detector arrays 14 undergo high-gain low-noise amplification and log conversion 17 before being converted to a digital value and recorded for analysis 18. The scatter measurement lasers 11 and 12 may be modulated or pulsed and the signal controlling the modulation or pulsing may be fed into the analog to digital conversion system 18. This information may be used to facilitate the removal of internal and external noise. The inclusion of a high-gain low-noise logarithmic amplifier allows for a high dynamic range signal to be compressed in a logarithmic fashion so more than ten decades of signal range can be easily converted and manage. Only some of the detectors 14 ever pass through the specular reflection (or transmission) 21 and most of the detectors 14 never pass through the specular reflection (or transmission) 21. This means that the available dynamic range of each detector 14 can be biased (up or down) so that the dynamic range of measurement available over the hemisphere exceeds ten decades.

The signal data is then analyzed by a computer analysis software 19 that converts the measurements to industry standard Bidirectional Reflectance Distribution Function (BRDF) and/or Bidirectional Transmittance Distribution Function (BTDF) which are jointly referred to as Bidirectional Scatter Distribution Function (BSDF). The computer software 19 provides multiple options for using and presenting the information including any combination of the following: a) three dimensional visualizations of the hemispherical scatter signal may be viewed, rotated, printed, and archived; b) virtual detectors may be defined by shape, size and angular location in software; the software will then compute the same signals as would be measured by a physical detector of any shape and location in the scatter hemisphere; and these measurements may be used directly or used to facilitate the design of optical instrumentation; c) scatter data may be exported in many formats to feed into other software such as optical modeling, lighting simulation, quality control, manufacturing control, etc.; d) depending on the sample, a variety of material characteristics may be characterized, including surface roughness, the surface power density function and the estimated sizes of discrete surface features such particles and pits; and e) a variety of optical characteristics may be calculated including haze, total integrated scatter, specular and diffuse reflectance, and specular and diffuse transmittance.

Any of these types of analysis can be used to generate numerical grades and, when provided with acceptable range values, can drive automated Pass/Fail inspection. Any of the scatter data, derived measurements, numerical grades and/or pass/fail analysis results may be used as feedback for control of scientific, manufacturing or other processes or for quality control inspection.

The present invention also includes methods for using the scatterometer 10. A first method for measuring the intensity of the specular reflection (or transmission) radiation 21 and scattered radiation 22 with a hemispherical scanning optical scatterometer 10, comprises directing a laser beam 20 from a reflected scatter measurement laser 11 at a sample 13 and/or directing a second laser beam 25 from a transmitted scatter measurement laser 12 at the sample; measuring the intensity of the specular reflection (or transmission) and light scattered by the sample 13 with an array of optical detectors 14 located on an arm 15; rotating the array of optical detectors 14 through a nearly complete hemisphere or a partial hemisphere of specular reflection (or transmission) and scattered light on a fixed path with a computer controlled system 16; performing a logarithmic conversion and amplification of the signal from the detectors 14 with an electronic system 17; converting the signal from digital to analog form with a computer interface 18; and processing the signal with a computer 19.

The first method for using the scatterometer 10 wherein the step of detecting with optical detectors 14 uses small diameter, high resolution detectors for scanning through the specular reflection (or transmission) 21 and region near the specular reflection (or transmission), and larger detectors for measuring scattered light farther away from the specular (or transmission) angle 22.

The first method for using the scatterometer 10 wherein the step of processing the signal with a computer 19 converts the measurements to Bidirectional Reflectance Distribution Function (BRDF) and/or Bidirectional Transmittance Distribution Function (BTDF) which are jointly referred to as Bidirectional Scatter Distribution Function (BSDF).

The first method for using the scatterometer 10 wherein the step of detecting the laser light uses optical detectors 14 each biased to work over a fixed sensitivity range.

The first method for using the scatterometer 10 wherein the step of detecting the laser light uses optical detectors 14 with an available dynamic range of more than ten decades over the hemisphere and the measurement speed for a sample 13 is about 1 to 10 seconds.

The first method for using the scatterometer 10 wherein the step of processing with a computer 19 produces a three dimensional visualization of the hemispherical scatter signal.

The first method for using the scatterometer 10 wherein the step of processing with a computer 19 characterizes material characteristics of the sample 13, such as surface roughness, the surface power spectral density function and estimated sizes of discrete surface features of the sample 13 such particles and pits.

The first method of using the scatterometer 10 wherein the step of processing with a computer 19 calculates optical characteristics such as haze, Total Integrated Scatter, specular and diffuse reflectance, and specular and diffuse transmittance.

The first method of using the scatterometer 10 wherein the step of processing with a computer 19 calculates scatter data, derived measurements, numerical grades and/or pass/fail analysis results for control of scientific processes, manufacturing processes or for quality control inspection.

A second method for measuring specular reflection (or transmission) radiation 21 and scattered radiation 22 with a hemispherical scanning optical scatterometer 10, comprises: directing a laser light 20 at a sample 13 at an incident angle from a scatter measurement laser 11 located on a first arm 23; detecting the laser light scattered by the sample 13 with an array of optical detectors 14 located on a second arm 15; rotating the array of optical detectors 14 through a nearly complete hemisphere or a partial hemisphere of specular reflection (or transmission) and scattered light on a fixed path with a computer controlled system 16; rotating the scatter measurement laser 11 to a plurality of incident angles with a second computer controlled system 24 and the measurement is repeated at those incident angles; performing a logarithmic conversion and amplification of the signal from the detectors 14 with a computer controlled system; converting the signal from digital to analog form with an electronic system 17; and processing the signal with a computer 19.

The second method of using the scatterometer 10 wherein the step of detecting with optical detectors 14 uses small diameter, high resolution detectors for scanning through the specular reflection (or transmission) 21 and the light scattered at angles close to that of the specular reflection (or transmission) (typically within 1/10 to 10 degrees), and larger detectors for measuring scattered light at a larger angular deviation from the specular reflection (or transmission) 22.

The second method of using the scatterometer 10 wherein the step of processing the signal with a computer 19 converts the measurements to Bidirectional Reflectance Distribution Function (BRDF) and/or Bidirectional Transmittance Distribution Function (BTDF) which are jointly referred to as Bidirectional Scatter Distribution Function (BSDF).

The second method of using the scatterometer 10 wherein the optical detectors 14 measure the intensity the signal at defined locations on their fixed paths.

The second method of using the scatterometer 10 wherein the step of measuring the intensity of the laser light uses optical detectors 14 each biased to work over a fixed sensitivity range.

The second method of using the scatterometer 10 wherein the step of measuring the intensity of the laser light uses optical detectors 14 with an available dynamic range of more than ten decades over the hemisphere and the measurement speed for a sample 13 is about 1 to 30 seconds.

The second method of using the scatterometer 10 wherein the step of processing with a computer 19 produces a three dimensional visualization of the hemispherical scatter signal.

The second method of using the scatterometer 10 wherein the step of processing with a computer 19 characterizes material characteristics of the sample 13, such as surface roughness, the surface power spectral density function and estimated sizes of discrete surface features of the sample 13 such particles and pits.

The second method of using the scatterometer 10 wherein the step of processing with a computer 19 calculates optical characteristics such as haze, Total Integrated Scatter, specular and diffuse reflectance, and specular and diffuse transmittance.

The second method of using the scatterometer 10 wherein the step of processing with a computer calculates scatter data, derived measurements, numerical grades and/or pass/fail analysis results for control of scientific processes, manufacturing processes or for quality control inspection.

The foregoing discussion discloses and describes merely exemplary embodiments of the present invention. The invention is not limited to the method and the apparatus as described in detail above. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. A hemispherical scanning optical scatterometer for measuring scattered radiation, the scatterometer comprising:
   one or more scatter measurement lasers, located on one or more source arms and directing laser light at a sample at one or more incident angles;
   an array of optical detectors located on a measurement arm and measuring an intensity of a signal from the laser light scattered by the sample in either reflectance or transmission;
   a first computer controlled system to rotate the source arm or arms through a complete or partial sphere about an axis horizontal to the sample;
   a second computer controlled system to rotate the measurement arm of optical detectors on fixed paths about the axis horizontal to the sample so that a specular beam and a complete scattering hemisphere can be adequately sampled, with the optical detectors remaining perpendicular to scattered rays being measured through an entire hemispherical scan, with the source arm rotating in a same direction as the measurement arm and with the source arm rotating through a larger radius than the measurement arm;
   electronic systems for signal processing of each optical detector that include amplification and/or logarithmic conversion;
   a computer interface for conversion of the signal from analog to digital form; and
   a computer for processing the signal.

2. The scatterometer of claim 1, wherein the optical detectors include small diameter, high resolution detectors for scanning through specular reflection (or transmission) and the region near the specular reflection (or transmission), and larger detectors for measuring scattered light farther away from the specular (or transmission) direction.

3. The scatterometer of claim 1, wherein the computer for processing the signal converts the measurements to Bidirectional Reflectance Distribution Function (BRDF) and/or Bidirectional Transmittance Distribution Function (BTDF) which are jointly referred to as Bidirectional Scatter Distribution Function (BSDF).

4. The scatterometer of claim 1, wherein the optical detectors measure the intensity of the signal at defined locations on their fixed paths.

5. The scatterometer of claim 1, wherein each of the optical detectors are biased to work over a fixed sensitivity range.

6. The scatterometer of claim 1, wherein the optical detectors have an available dynamic range of more than ten decades over the hemisphere and the measurement speed for a sample is about 1 to 30 seconds.

7. The scatterometer of claim 1, wherein the computer for processing the signal produces a three dimensional visualization of the hemispherical scatter signal.

8. The scatterometer of claim 1, wherein the computer for processing the signal characterizes material characteristics of the sample, such as surface roughness, the surface power spectral density function and/or estimated sizes of discrete features of the sample such particles and pits.

9. The scatterometer of claim 1, wherein the computer for processing the signal calculates optical characteristics such as haze, Total Integrated Scatter, specular and diffuse reflectance, and/or specular and diffuse transmittance.

10. The scatterometer of claim 1, wherein the computer for processing the signal calculates scatter data, derived measurements, numerical grades and/or pass/fail analysis results for control of scientific processes, manufacturing processes or for quality control inspection.

11. A method for measuring scattered radiation with a hemispherical scanning optical scatterometer, comprising:
    directing one or more lasers at a sample at one or more incident angles from a scatter measurement laser located on one or more source arms, rotating through a complete or partial sphere, about an axis horizontal to the sample;
    measuring intensities of the laser light scattered by the sample in either reflectance or transmission with an array of optical detectors located on a measurement arm;
    rotating the array of optical detectors on fixed paths about the axis horizontal to the sample with a first computer controlled system so that a specular beam and a complete scattering hemisphere can be adequately sampled, rotating the optical detectors perpendicular to scattered rays being measured through an entire hemispherical scan, rotating the source arm in a same direction as the measurement arm and rotating the source arm through a larger radius than the measurement arm;
    rotating the scatter measurement laser or lasers with a second computer controlled system through a plurality of incident angles;
    measuring repeatedly at the plurality of incident angles;
    performing processing of the signals from the detectors that include logarithmic conversion and/or amplification with an electronic system;
    converting the signal from analog to digital form with a computer interface; and
    processing the signal with a computer.

12. The method of claim 11, wherein the step of measuring intensities with optical detectors uses small diameter, high resolution detectors for scanning through specular reflection (or transmission) and the region near the specular reflection (or transmission), and larger detectors for measuring scattered light farther away from the specular (or transmission) direction.

13. The method of claim 11, wherein the step of processing the signals with a computer converts the measurements to Bidirectional Reflectance Distribution Function (BRDF) and/or Bidirectional Transmittance Distribution Function (BTDF) which are jointly referred to as Bidirectional Scatter Distribution Function (BSDF).

14. The scatterometer of claim 11, wherein the step of measuring intensities uses optical detectors measuring the intensity of the signal at defined locations on their fixed paths.

15. The method of claim 11, wherein the step of measuring the intensity of the laser light uses optical detectors each biased to work over a fixed sensitivity range.

16. The method of claim 11, wherein the step of measuring the intensity of the laser light uses optical detectors with an available dynamic range of more than ten decades over the hemisphere and the measurement speed for a sample is about 1 to 30 seconds.

17. The method of claim 11, wherein the step of processing with a computer produces a three dimensional visualization of the hemispherical scatter signal.

18. The method of claim 11, wherein the step of processing with a computer characterizes material characteristics of the sample, such as surface roughness, the surface power spectral density function and/or estimated sizes of discrete surface features of the sample such particles and pits.

19. The method of claim 11, wherein the step of processing with a computer calculates optical characteristics such as haze, Total Integrated Scatter, specular and diffuse reflectance, and/or specular and diffuse transmittance.

20. The method of claim 11, wherein the step of processing with a computer calculates scatter data, derived measurements, numerical grades and/or pass/fail analysis results for control of scientific processes, manufacturing processes or for quality control inspection.

* * * * *